(12) United States Patent
Rahmer et al.

(10) Patent No.: US 10,168,408 B2
(45) Date of Patent: Jan. 1, 2019

(54) MPI APPARATUS WITH FAST FIELD OF VIEW MOTION

(71) Applicant: KONINKLIJKE PHILIPS N.V., Eindhoven (NL)

(72) Inventors: Jurgen Erwin Rahmer, Eindhoven (NL); Bernhard Gleich, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 321 days.

(21) Appl. No.: 14/917,598

(22) PCT Filed: Sep. 11, 2013

(86) PCT No.: PCT/IB2013/058456
§ 371 (c)(1),
(2) Date: Mar. 9, 2016

(87) PCT Pub. No.: WO2015/036814
PCT Pub. Date: Mar. 19, 2015

(65) Prior Publication Data
US 2016/0216355 A1    Jul. 28, 2016

(51) Int. Cl.
*G01R 33/565* (2006.01)
*A61B 5/05* (2006.01)
*G01R 33/12* (2006.01)

(52) U.S. Cl.
CPC ...... *G01R 33/56509* (2013.01); *A61B 5/0515* (2013.01); *G01R 33/1276* (2013.01)

(58) Field of Classification Search
None
See application file for complete search history.

(56) References Cited

U.S. PATENT DOCUMENTS

| 6,067,465 A | 5/2000 | Foo et al. |
| 2011/0089942 A1* | 4/2011 | Goodwill ............... A61B 5/05 324/301 |

(Continued)

FOREIGN PATENT DOCUMENTS

| DE | 10151778 A1 | 5/2003 |
| EP | 1224542 A2 | 7/2002 |

(Continued)

OTHER PUBLICATIONS

Gleich et al, "Tomographic Imaging Using the Nonlinear Response of Magnetic Particles" Nature , vol. 435 pp. 1214-1217.

(Continued)

*Primary Examiner* — Patrick Assouad
*Assistant Examiner* — Demetrius Pretlow

(57) ABSTRACT

The present invention relates to an apparatus (100) for influencing and/or detecting magnetic particles in a field of view (28), in particular an MPI apparatus. The apparatus comprises selection field elements (116) for generating a magnetic selection field (50), drive field coils (124; 125, 126, 127) for changing the position in space of the two sub-zones (52, 54) by means of a magnetic drive field, focus field elements (116) for changing the position in space of the field of view (28) by means of a magnetic focus field, and receiving elements (148) for acquiring detection signals. A static system function of the apparatus is obtained in the absence of a magnetic focus field, from which an extended system function is generated by shifting a time-domain representation of said static system function proportional to the changes of the position of the field of view caused by appliance of the magnetic focus field. Said extended system function is then used for reconstructing the spatial distribution of the magnetic particles in the field of view from the detection signals.

21 Claims, 7 Drawing Sheets

(56) References Cited

U.S. PATENT DOCUMENTS

| | | | |
|---|---|---|---|
| 2011/0098558 A1* | 4/2011 | Weaver | A61B 5/05 600/420 |
| 2011/0221438 A1 | 9/2011 | Goodwill et al. | |
| 2012/0126808 A1* | 5/2012 | Knopp | A61B 5/0515 324/301 |
| 2012/0153948 A1* | 6/2012 | Rahmer | A61B 5/05 324/301 |
| 2012/0153949 A1* | 6/2012 | Biederer | A61B 5/05 324/301 |
| 2015/0276902 A1* | 10/2015 | Weaver | G01R 33/1276 324/309 |

FOREIGN PATENT DOCUMENTS

| | | |
|---|---|---|
| WO | 2004091386 | 10/2004 |
| WO | 2004091390 | 10/2004 |
| WO | 2004091394 | 10/2004 |
| WO | 2004091395 A2 | 10/2004 |
| WO | 2004091396 | 10/2004 |
| WO | 2004091397 | 10/2004 |
| WO | 2004091398 | 10/2004 |
| WO | 2004091408 A2 | 10/2004 |
| WO | 2010067248 A1 | 6/2010 |
| WO | 2010067264 A1 | 6/2010 |
| WO | 2012046157 A1 | 4/2012 |

OTHER PUBLICATIONS

Rahmer et al "Continuous Focus Field Varation for Extending the Imaging Range in 3D MPI". . . 140 (2012) p. 255.

Gruettner et al "ID-Image Reconstruction for Magnetic Particle Imaging Using a Hybrid System Function" Nuclear Science Symposium and Medical Imaging Conf. Oct. 23, 2011 p. 2545-2548.

Rahmer et al, "Fast Continuous Motion of the Field of View in Magnetic Imaging" IEEE Mar. 23, 2013 p. 1.

Goodwill et al "Multidimensional X-Space Magnetic Particle Imaging" IEEE Transactions on Medical Imaging vol. 30, No. 9, Sep. 2011.

Gleich et al "Fast MPI Demonstrator With Enlarged Field of View" Proc. Intl. Soc. Mag. Resona Med. 18 (2010).

Rahmer et al "Results on Rapid 3D Magnetic Particle Imaging With a Large Field of View" Proc. Intl. Soc. Mag. Reson. Med. 19 (2011) p. 629.

\* cited by examiner

1st frame intermediate frame last frame

MPI APPARATUS WITH FAST FIELD OF VIEW MOTION

CROSS-REFERENCE TO PRIOR APPLICATIONS

This application is the U.S. National Phase application under 35 U.S.C. § 371 of International Application No. PCT/IB2013/058456, filed on Sep. 11, 2014. This application is incorporated by reference herein.

FIELD OF THE INVENTION

The present invention relates to an apparatus and method for influencing and/or detecting magnetic particles in a field of view, in particular a magnetic particle imaging apparatus that allows fast field of view motions.

BACKGROUND OF THE INVENTION

Magnetic Particle Imaging (MPI) is an emerging medical imaging modality. The first versions of MPI were two-dimensional in that they produced two-dimensional images. Newer versions are three-dimensional (3D). A four-dimensional image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, an MP image of an object's volume of interest is generated in two steps. The first step, referred to as data acquisition, is performed using an MPI scanner. The MPI scanner is arranged to generate a static magnetic gradient field, called the "selection field", which has a (single or more) field-free point(s) (FFP(s)) or a field-free line (FFL) at the isocenter of the scanner. Moreover, this FFP (or the FFL; mentioning "FFP" in the following shall generally be understood as meaning FFP or FFL) is surrounded by a first sub-zone with a low magnetic field strength, which is in turn surrounded by a second sub-zone with a higher magnetic field strength. In addition, the scanner has means to generate a time-dependent, spatially nearly homogeneous magnetic field. Actually, this field is obtained by superposing a rapidly changing field with a small amplitude, called the "drive field", and a slowly varying field with a large amplitude, called the "focus field". By adding the time-dependent drive and focus fields to the static selection field, the FFP may be moved along a predetermined FFP trajectory throughout a "volume of scanning" surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning.

The object must contain magnetic nanoparticles or other magnetic non-linear materials; if the object is an animal or a patient, a tracer containing such particles is administered to the animal or patient prior to the scan. During the data acquisition, the MPI scanner moves the FFP along a deliberately chosen trajectory that traces out/covers the volume of scanning, or at least the field of view. The magnetic nanoparticles within the object experience a changing magnetic field and respond by changing their magnetization. The changing magnetization of the nanoparticles induces a time-dependent voltage in each of the receive coils. This voltage is sampled in a receiver associated with the receive coil. The samples output by the receivers are recorded and constitute the acquired data. The parameters that control the details of the data acquisition make up the "scan protocol".

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model can be formulated as an integral operator that acts on the acquired data; the reconstruction algorithm tries to undo, to the extent possible, the action of the model.

Such an MPI apparatus and method have the advantage that they can be used to examine arbitrary examination objects—e.g. human bodies—in a non-destructive manner and with a high spatial resolution, both close to the surface and remote from the surface of the examination object. Such an apparatus and method are generally known and have been first described in DE 101 51 778 A1 and in Gleich, B. and Weizenecker, J. (2005), "Tomographic imaging using the nonlinear response of magnetic particles" in Nature, vol. 435, pp. 1214-1217, in which also the reconstruction principle is generally described. The apparatus and method for magnetic particle imaging (MPI) described in that publication take advantage of the non-linear magnetization curve of small magnetic particles.

In contrast to established imaging modalities like MRI and CT, no simple mathematical transform has yet been identified for MPI to reconstruct images from the acquired data. Therefore, MPI image reconstruction requires knowledge of a "system function" describing the system response to a given spatial distribution of particles, i.e., mapping particle position to frequency response. To solve the reconstruction problem, the system function has to be inverted, usually requiring some regularization scheme.

The system function can be determined experimentally by measuring the magnetization response of a point-like sample at a large number of spatial positions corresponding to the number of image pixels or voxels. This calibration procedure requires quite long acquisition times, in particular in order to obtain a reasonable signal-to-noise ratio (SNR). More details with respect to the acquisition, features and use of the system function as well as preferred embodiment for faster acquisition and for reducing the storage space for storing the system function can be found in WO 2010/067248 A1 and WO 2010/067264 A1, which details are herein incorporated by reference.

Large spatial coverage in MPI can be achieved by moving the field of view (FOV) encoded by magnetic drive fields using additional homogeneous offset fields called magnetic focus fields. To date, magnetic focus fields have been applied e.g. to generate a slow continuous FOV motion with 3D encoding as described in J. Rahmer et al., "Continuous Focus Field Variation for Extending the Imaging Range in 3D MPI", Magnetic Particle Imaging: A Novel SPIO Nanoparticle Imaging Technique 140 (2012): 255. For a continuous FOV motion during imaging, "slow" means that the shift during one encoding period remains below the reconstructed spatial resolution. In the above mentioned paper of J. Rahmer, an uncompromised image quality was demonstrated for a shift velocity of about 20 mm/s, which is sufficiently far below the 50 mm/s that correspond to the ratio between the 3D encoding time of 21.5 ms and the resolution of roughly 1 mm.

SUMMARY OF THE INVENTION

It is an object of the present invention to provide an apparatus and method for influencing and/or detecting magnetic particles in a field of view, i.e. an MPI apparatus, that enables reconstruction of images with no or reduced motion artifacts even in case of fast coverage of imaging volumes (i.e. much larger than the volume covered by the magnetic drive field excitation) by use of rapid magnetic focus field variations.

In a first aspect of the present invention an apparatus for influencing and/or detecting magnetic particles in a field of view is presented comprising:

selection elements comprising a selection field signal generator unit and selection field elements for generating a magnetic selection field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view, drive elements comprising a drive field signal generator unit and drive field coils for changing the position in space of the two sub-zones in the field of view by means of a magnetic drive field so that the magnetization of the magnetic material changes locally, focus elements comprising a focus field signal generator unit and focus field elements for changing the position in space of the field of view by means of a magnetic focus field, receiving elements for acquiring detection signals, which detection signals depend on the magnetization in the field of view, which magnetization is influenced by the change in the position in space of the first and second sub-zone, storage elements for storing a static system function of the apparatus obtained in the absence of a magnetic focus field, processing elements for generating an extended system function by shifting a time-domain representation of said static system function proportional to the changes of the position of the field of view caused by appliance of the magnetic focus field and for reconstructing the spatial distribution of the magnetic particles in the field of view from the detection signals and the extended system function.

In a second aspect of the present invention an apparatus for influencing and/or detecting magnetic particles in a field of view is presented comprising:

selection elements comprising a selection field signal generator unit and selection field elements for generating a magnetic selection field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view, drive elements comprising a drive field signal generator unit and drive field coils for changing the position in space of the two sub-zones in the field of view by means of a magnetic drive field so that the magnetization of the magnetic material changes locally, focus elements comprising a focus field signal generator unit and focus field elements for changing the position in space of the field of view by means of a magnetic focus field, receiving elements for acquiring detection signals, which detection signals depend on the magnetization in the field of view, which magnetization is influenced by the change in the position in space of the first and second sub-zone, storage elements for storing a plurality of static and/or extended system functions of the apparatus, wherein the static system functions have been obtained in the absence of a magnetic focus field at different positions of the field of view and the extended system functions have been generated by shifting the time-domain representation of a static system function proportional to different changes of the position of the field of view caused by appliance of different magnetic focus fields or have been obtained while different changes of the position of the field of view are caused by appliance of different magnetic focus fields, and processing elements for reconstructing the spatial distribution of the magnetic particles in the field of view from the detection signals and an extended system function selected or constructed from the stored plurality of static and/or extended system functions based on the magnetic focus field applied for changing the position in space of the field of view.

In a further aspect of the present invention corresponding methods are presented.

Preferred embodiments of the invention are defined in the dependent claims. It shall be understood that the claimed apparatus and methods have similar and/or identical preferred embodiments as defined in the dependent claims.

The present invention is based on the idea to modify the system function, which is typically acquired in the absence of variable magnetic focus fields and stored in the frequency domain representation. This "static" system function is transformed into the temporal domain, e.g. via Fourier transformation. Sequential volumes representing different times during the field-free point sequence (i.e. the trajectory) then are shifted according to the FFP shift induced by the variable magnetic focus fields. Afterwards, the static system function is transformed back to the frequency domain where the standard reconstruction procedure is applied.

Fast coverage of large spatial volumes in MPI requires rapid changes in the magnetic focus fields which enact rapid shifts of the FOV. If these occur during the imaging process, motion artifacts arise. With the proposed compensation technique, either deliberate FOV motion or unwanted motion due to residual eddy currents can be compensated in image reconstruction, as long as the temporal evolution of additional magnetic fields is known. Thus, according to the present invention, for high FOV velocities up to several hundred mm/s motion artifacts can be reduced by the proposed addition of linear shift to the time-domain representation of the system function used for image reconstruction.

According to the first aspect only the static system function of the apparatus, which has been obtained in advance without applying any magnetic focus fields (hence the name "static system function"), is stored. During or after the real data acquisition of detection signals the extended system function is generated by use of the information about the changes of the field of view caused by the magnetic focus fields. Thus, a system function covering a larger volume (hence the name "extended system function") is obtained, which is then used for the reconstruction of the desired image (i.e. for reconstructing the spatial distribution of the magnetic particles in the field of view) from the detection signals in the larger volume.

For combining (concatenating) the shifted system functions several options are generally available. One option is to create a large system function that comprises all movement patterns. The reconstruction then provides the complete image. However, the extended system function may become quite large. Another option is to reconstruct small sub-volumes (typically according to one Lissajous period) which are combined later into the complete image. For overlapping areas a weighting may be applied, which decreases towards the edges of the respective data set.

According to the second aspect a plurality of static and/or extended system functions of the apparatus, which have been obtained in advance while no magnetic focus fields (for obtaining static system functions for different positions of the field of view) or different magnetic focus fields (for obtaining extended system functions) have been applied, are stored. During or after the real data acquisition of detection signals the static and/or extended system function is selected or constructed from the plurality of stored static and/or extended system functions that as much as possible corresponds to the magnetic focus field that is actually applied during the acquisition of the detection signals. In other words, in one embodiment the stored extended system function is selected which has been generated while a magnetic focus field has been applied that as much as possible corresponds to the magnetic focus field that is actually applied during the acquisition of detection signals. In another embodiment, the extended system function is constructed from one or more of the stored static and/or extended system functions.

In a preferred embodiment of the apparatus according to the first aspect the storage elements is configured to store a frequency-domain representation of the static system function and the processing elements is configured to convert the frequency-domain representation of the static system function into the time-domain representation before shifting the time-domain representation of the static system function to generate the extended system function and to convert the extended system function into a frequency-domain representation used for reconstructing the spatial distribution of the magnetic particles. Thus, the spatial shift of the static system function is performed in the time domain, while the system function is preferably stored in the frequency domain, and is also used in the frequency domain for reconstructing an image.

The data are measured in the time domain and may generally also be stored in the time domain, but storing them in the frequency domain is more advantageous for background correction and data processing, e.g. in case of filtering. Further, unnecessary frequency components can be discarded from processing and need not to be stored.

Preferably, the apparatus according to the first aspect further comprises measurement means for measuring the magnetic focus field, wherein said processing elements is configured to use the measured magnetic focus field for shifting the time-domain representation of said static system function proportional to the changes of the position of the field of view caused by the measured magnetic focus field. While generally the apparatus knows which magnetic focus field is applied and, thus, how the field of view is shifted, measuring the magnetic focus field and using the information from this measurement for spatially shifting the static system function may further increase the accuracy of the shift, the obtained extended system function and, thus, of the reconstructed image. Said measurement means preferably comprises a Hall sensor or any other sensor that can measure a magnetic field. Through this measurement dynamic eddy current effects may be measured which can then be compensated.

In another preferred embodiment of the apparatus according to the first aspect said processing elements is configured to generate the extended system function by padding in the direction of motion of the magnetic focus field, wherein padded voxels (of the larger volume obtained by shifting the static system function) are filled with zeros or with extrapolated values of the values of neighboring voxels, where the extrapolation procedure can also rely on simulated data.

In a preferred embodiment of the apparatus according to the second aspect an extended system function is generated by shifting a time-domain representation of a static system function of the apparatus obtained in the absence of a magnetic focus field proportional to the changes of the position of the field of view caused by appliance of the magnetic focus field.

Preferably, the apparatus according to the second aspect further comprises measurement means for measuring the magnetic focus field, wherein said processing elements is configured to use the measured magnetic focus field for selecting or constructing an extended system function from the stored plurality of static and/or extended system functions. As explained above for the apparatus according to the first aspect, this may increase the accuracy. Again, said measurement means preferably comprises a Hall sensor or any other sensor that can measure a magnetic field.

In another preferred embodiment of the apparatus according to the second aspect the storage elements is configured to store a plurality of extended system functions that have been obtained for different speeds of movement of the first sub-zone, different directions of movement of the first sub-zone and/or different trajectories along which the first sub-zone is moved. Thus, a catalogue of various extended system functions is stored that allow selection or construction of an extended system function that fits as much as possible to an actual shift of the field of view by use of the magnetic focus field, leading to an increase of accuracy of the reconstructed images.

The changes of the position of the field of view caused by appliance of the magnetic focus field compensated by shifting a time-domain representation of said static system function preferably include one or more of a linear shift motion, an accelerated motion, a decelerated motion and a curved motion. Hence, generally all different kinds of motion of the field of view caused by the magnetic focus field may be compensated according to the present invention.

According to an embodiment the processing elements is configured to shift the starting and/or end point of a reconstructed trajectory, wherein different time shifts can be reconstructed, and to concatenate shifted extended system functions. In this way the quality of the reconstruction can be improved and it can also enable to reconstruct larger volumes.

According to another embodiment the processing elements is configured to determine the size and position of the largest gaps between paths of the trajectory covered by the first sub-zone, i.e. the FFP. This may appear if the additional shift of the FFP due to the focus fields is too fast so that a warning can be issued to the user to reduce the speed of the shift to avoid degradation of the quality of the reconstruction.

In still another embodiment said processing elements is configured to apply a distortion correction to the reconstructed spatial distribution of the magnetic particles. In this way, the quality of the reconstructed images can be further increased.

The processing elements is preferably configured to apply an amplitude correction of the amplitude of the extended system function based on the velocity of the movement of the first sub-zone during appliance of the magnetic focus field. This compensates for slight modifications in amplitude of the spatial signal response patterns caused by the addition of the magnetic focus field to the magnetic drive fields when compared with the system function that was acquired without focus fields, and thus further increases the quality of reconstructed images. Generally, not the complete extended system function is amplitude corrected, but each time step is amplitude corrected separately.

In one embodiment the focus field means and the selection elements are implemented by separate elements, i.e. separate coils and/or separate generator units. In another embodiment MPI apparatus employs combined selection-and-focus field coils (and, preferably, a combined generator unit), which is based on the idea to combine focus field coils and the selection field coils that are generally provided as separate coils in the known MPI apparatus into a combined set of selection-and-focus field coils. Hence, a single current is provided to each of said coils rather than separate currents as conventionally provided to each focus field coil and each selection field coil. The single currents can thus be regarded as two superposed currents for focus field generation and selection field generation. The desired location and movement of the field of view within the examination area can be easily changed by controlling the currents to the various coils. Not all selection-and-focus field coils must, however, always be provided with control currents, but some coils are only needed for certain movements of the field of view.

The proposed embodiment using combined selection-and-focus field coils further provides more freedom of how and where to arrange the coils with respect to the examination area in which the subject is place. It is particularly possible with this arrangement to build an open scanner that is easily accessible both by the patient and by doctors or medical personnel, e.g. a surgeon during an intervention.

The drive field coils are preferably arranged in the area between said first inner selection-and-focus field coils of the twos sets of selection-and-focus field coils. The drive field coils may be designed such that they are (fixedly or movable) arranged between the two sets of selection-and-focus field coils. In other embodiments, the drive field coils are somewhat flexible and can be arranged on the desired portion of the patient's body before the patient is placed inside the examination area.

With such an embodiment the magnetic gradient field (i.e. the magnetic selection field) is generated with a spatial distribution of the magnetic field strength such that the field of view comprises a first sub-area with lower magnetic field strength (e.g. the FFP), the lower magnetic field strength being adapted such that the magnetization of the magnetic particles located in the first sub-area is not saturated, and a second sub-area with a higher magnetic field strength, the higher magnetic field strength being adapted such that the magnetization of the magnetic particles located in the second sub-area is saturated. Due to the non-linearity of the magnetization characteristic curve of the magnetic particles the magnetization and thereby the magnetic field generated by the magnetic particles shows higher harmonics, which, for example, can be detected by a detection coil. The evaluated signals (the higher harmonics of the signals) contain information about the spatial distribution of the magnetic particles, which again can be used e.g. for medical imaging, for the visualization of the spatial distribution of the magnetic particles and/or for other applications.

The MPI apparatus according to the present invention are based on a new physical principle (i.e. the principle referred to as MPI) that is different from other known conventional medical imaging techniques, as for example nuclear magnetic resonance (NMR). In particular, this new MPI-principle, does, in contrast to NMR, not exploit the influence of the material on the magnetic resonance characteristics of protons, but rather directly detects the magnetization of the magnetic material by exploiting the non-linearity of the magnetization characteristic curve. In particular, the MPI-technique exploits the higher harmonics of the generated magnetic signals which result from the non-linearity of the magnetization characteristic curve in the area where the magnetization changes from the non-saturated to the saturated state.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in detail with reference to FIGS. 1 to 4. In particular, four embodiments of an MPI scanner for medical diagnostics will be described. An informal description of the data acquisition will also be given. The similarities and differences between the different embodiments will be pointed out. Generally, the present invention can be used in all these different embodiments of an MPI apparatus.

Figure 1:
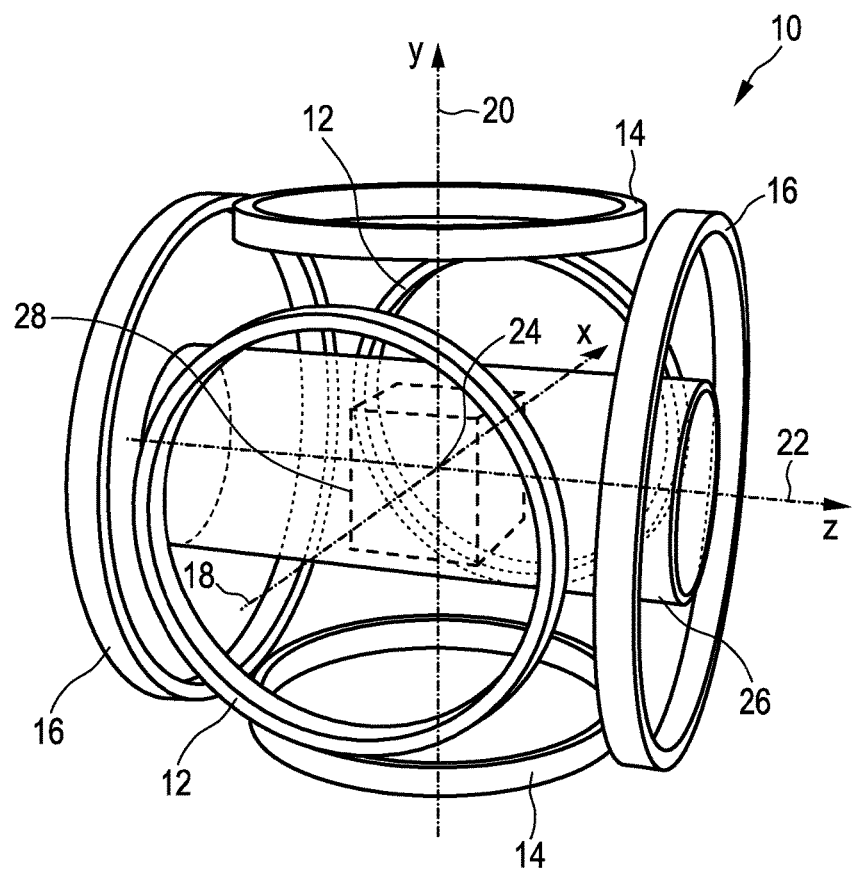
FIG. 1 shows a first embodiment of an MPI apparatus.

The first embodiment 10 of an MPI scanner shown in FIG. 1 has three pairs 12, 14, 16 of coaxial parallel circular coils, these coil pairs being arranged as illustrated in FIG. 1. These coil pairs 12, 14, 16 serve to generate the selection field as well as the drive and focus fields. The axes 18, 20, 22 of the three coil pairs 12, 14, 16 are mutually orthogonal and meet in a single point, designated the isocenter 24 of the MPI scanner 10. In addition, these axes 18, 20, 22 serve as the axes of a 3D Cartesian x-y-z coordinate system attached to the isocenter 24. The vertical axis 20 is nominated the y-axis, so that the x- and z-axes are horizontal. The coil pairs 12, 14, 16 are named after their axes. For example, the y-coil pair 14 is formed by the coils at the top and the bottom of the scanner. Moreover, the coil with the positive (negative)

y-coordinate is called the y⁺-coil (y⁻-coil), and similarly for the remaining coils. When more convenient, the coordinate axes and the coils shall be labelled with $x_1$, $x_2$, and $x_3$, rather than with x, y, and z.

The scanner 10 can be set to direct a predetermined, time-dependent electric current through each of these coils 12, 14, 16, and in either direction. If the current flows clockwise around a coil when seen along this coil's axis, it will be taken as positive, otherwise as negative. To generate the static selection field, a constant positive current $I^S$ is made to flow through the z⁺-coil, and the current $-I^S$ is made to flow through the z⁻-coil. The z-coil pair 16 then acts as an anti-parallel circular coil pair.

It should be noted here that the arrangement of the axes and the nomenclature given to the axes in this embodiment is just an example and might also be different in other embodiments. For instance, in practical embodiments the vertical axis is often considered as the z-axis rather than the y-axis as in the present embodiment. This, however, does not generally change the function and operation of the device and the effect of the present invention.

Figure 2:
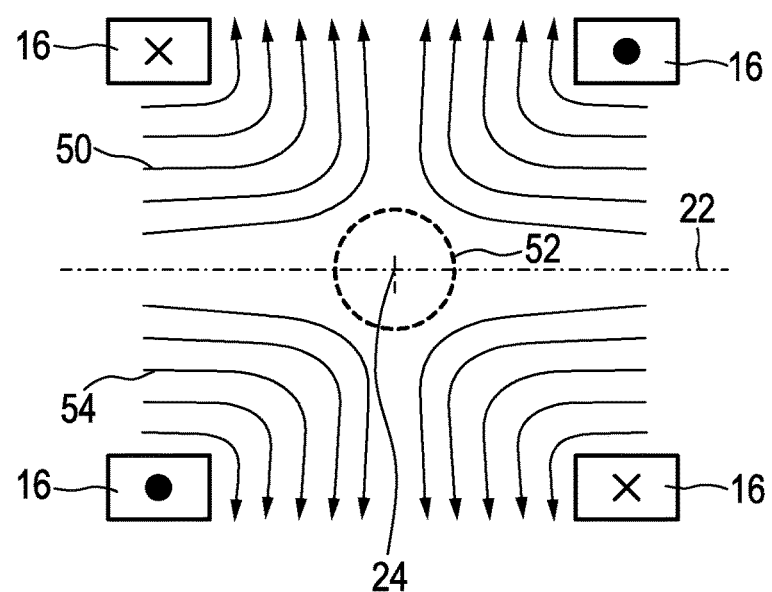
FIG. 2 shows an example of the selection field pattern produced by an apparatus as shown in FIG. 1.

The magnetic selection field, which is generally a magnetic gradient field, is represented in FIG. 2 by the field lines 50. It has a substantially constant gradient in the direction of the (e.g. horizontal) z-axis 22 of the z-coil pair 16 generating the selection field and reaches the value zero in the isocenter 24 on this axis 22. Starting from this field-free point (not individually shown in FIG. 2), the field strength of the magnetic selection field 50 increases in all three spatial directions as the distance increases from the field-free point. In a first sub-zone or region 52 which is denoted by a dashed line around the isocenter 24 the field strength is so small that the magnetization of particles present in that first sub-zone 52 is not saturated, whereas the magnetization of particles present in a second sub-zone 54 (outside the region 52) is in a state of saturation. In the second sub-zone 54 (i.e. in the residual part of the scanner's field of view 28 outside of the first sub-zone 52) the magnetic field strength of the selection field is sufficiently strong to keep the magnetic particles in a state of saturation.

By changing the position of the two sub-zones 52, 54 (including the field-free point) within the field of view 28 the (overall) magnetization in the field of view 28 changes. By determining the magnetization in the field of view 28 or physical parameters influenced by the magnetization, information about the spatial distribution of the magnetic particles in the field of view 28 can be obtained. In order to change the relative spatial position of the two sub-zones 52, 54 (including the field-free point) in the field of view 28, further magnetic fields, i.e. the magnetic drive field, and, if applicable, the magnetic focus field, are superposed to the selection field 50.

To generate the drive field, a time dependent current $I^D_1$ is made to flow through both x-coils 12, a time dependent current $I^D_2$ through both y-coils 14, and a time dependent current $I^D_3$ through both z-coils 16. Thus, each of the three coil pairs acts as a parallel circular coil pair. Similarly, to generate the focus field, a time dependent current $I^F_1$ is made to flow through both x-coils 12, a current $I^F_2$ through both y-coils 14, and a current $I^F_3$ through both z-coils 16.

It should be noted that the z-coil pair 16 is special: It generates not only its share of the drive and focus fields, but also the selection field (of course, in other embodiments, separate coils may be provided). The current flowing through the z⁺-coil is $I^D_3 + I^F_3 \pm I^S$. The current flowing through the remaining two coil pairs 12, 14 is $I^D_k + I^F_k$, k=1, 2. Because of their geometry and symmetry, the three coil pairs 12, 14, 16 are well decoupled. This is wanted.

Being generated by an anti-parallel circular coil pair, the selection field is rotationally symmetric about the z-axis, and its z-component is nearly linear in z and independent of x and y in a sizeable volume around the isocenter 24. In particular, the selection field has a single field-free point (FFP) at the isocenter. In contrast, the contributions to the drive and focus fields, which are generated by parallel circular coil pairs, are spatially nearly homogeneous in a sizeable volume around the isocenter 24 and parallel to the axis of the respective coil pair. The drive and focus fields jointly generated by all three parallel circular coil pairs are spatially nearly homogeneous and can be given any direction and strength, up to some maximum strength. The drive and focus fields are also time-dependent. The difference between the focus field and the drive field is that the focus field varies slowly in time and may have a large amplitude, while the drive field varies rapidly and has a small amplitude. There are physical and biomedical reasons to treat these fields differently. A rapidly varying field with a large amplitude would be difficult to generate and potentially hazardous to a patient.

In a practical embodiment the FFP can be considered as a mathematical point, at which the magnetic field is assumed to be zero. The magnetic field strength increases with increasing distance from the FFP, wherein the increase rate might be different for different directions (depending e.g. on the particular layout of the device). As long as the magnetic field strength is below the field strength required for bringing magnetic particles into the state of saturation, the particle actively contributes to the signal generation of the signal measured by the device; otherwise, the particles are saturated and do not generate any signal.

The embodiment 10 of the MPI scanner has at least one further pair, preferably three further pairs, of parallel circular coils, again oriented along the x-, y-, and z-axes. These coil pairs, which are not shown in FIG. 1, serve as receive coils. As with the coil pairs 12, 14, 16 for the drive and focus fields, the magnetic field generated by a constant current flowing through one of these receive coil pairs is spatially nearly homogeneous within the field of view and parallel to the axis of the respective coil pair. The receive coils are supposed to be well decoupled. The time-dependent voltage induced in a receive coil is amplified and sampled by a receiver attached to this coil. More precisely, to cope with the enormous dynamic range of this signal, the receiver samples the difference between the received signal and a reference signal. The transfer function of the receiver is non-zero from zero Hertz ("DC") up to the frequency where the expected signal level drops below the noise level. Alternatively, the MPI scanner has no dedicated receive coils. Instead the drive field transmit coils are used as receive coils as is the case according to the present invention using combined drive-receiving coils.

The embodiment 10 of the MPI scanner shown in FIG. 1 has a cylindrical bore 26 along the z-axis 22, i.e. along the axis of the selection field. All coils are placed outside this bore 26. For the data acquisition, the patient (or object) to be imaged is placed in the bore 26 such that the patient's volume of interest—that volume of the patient (or object) that shall be imaged—is enclosed by the scanner's field of view 28—that volume of the scanner whose contents the scanner can image. The patient (or object) is, for instance, placed on a patient table. The field of view 28 is a geometrically simple, isocentric volume in the interior of the bore 26, such as a cube, a ball, a cylinder or an arbitrary shape. A cubical field of view 28 is illustrated in FIG. 1.

The size of the first sub-zone 52 is dependent on the strength of the gradient of the magnetic selection field and on the field strength of the magnetic field required for saturation, which in turn depends on the magnetic particles. For a sufficient saturation of typical magnetic particles at a magnetic field strength of 80 A/m and a gradient (in a given space direction) of the field strength of the magnetic selection field amounting to $50 \times 10^3$ A/m$^2$, the first sub-zone 52 in which the magnetization of the particles is not saturated has dimensions of about 1 mm (in the given space direction).

The patient's volume of interest is supposed to contain magnetic nanoparticles. Prior to the diagnostic imaging of, for example, a tumor, the magnetic particles are brought to the volume of interest, e.g. by means of a liquid comprising the magnetic particles which is injected into the body of the patient (object) or otherwise administered, e.g. orally, to the patient.

Generally, various ways for bringing the magnetic particles into the field of view exist. In particular, in case of a patient into whose body the magnetic particles are to be introduced, the magnetic particles can be administered by use of surgical and non-surgical methods, and there are both methods which require an expert (like a medical practitioner) and methods which do not require an expert, e.g. can be carried out by laypersons or persons of ordinary skill or the patient himself/herself. Among the surgical methods there are potentially non-risky and/or safe routine interventions, e.g. involving an invasive step like an injection of a tracer into a blood vessel (if such an injection is at all to be considered as a surgical method), i.e. interventions which do not require considerable professional medical expertise to be carried out and which do not involve serious health risks. Further, non-surgical methods like swallowing or inhalation can be applied.

Generally, the magnetic particles are pre-delivered or pre-administered before the actual steps of data acquisition are carried out. In embodiments, it is, however, also possible that further magnetic particles are delivered/administered into the field of view.

An embodiment of magnetic particles comprises, for example, a spherical substrate, for example, of glass which is provided with a soft-magnetic layer which has a thickness of, for example, 5 nm and consists, for example, of an iron-nickel alloy (for example, Permalloy). This layer may be covered, for example, by means of a coating layer which protects the particle against chemically and/or physically aggressive environments, e.g. acids. The magnetic field strength of the magnetic selection field 50 required for the saturation of the magnetization of such particles is dependent on various parameters, e.g. the diameter of the particles, the used magnetic material for the magnetic layer and other parameters.

In the case of e.g. a diameter of 10 µm with such magnetic particles, a magnetic field of approximately 800 A/m (corresponding approximately to a flux density of 1 mT) is then required, whereas in the case of a diameter of 100 µm a magnetic field of 80 A/m suffices. Even smaller values are obtained when a coating of a material having a lower saturation magnetization is chosen or when the thickness of the layer is reduced.

In practice, magnetic particles commercially available under the trade name Resovist (or similar magnetic particles) are often used, which have a core of magnetic material or are formed as a massive sphere and which have a diameter in the range of nanometers, e.g. 40 or 60 nm.

For further details of the generally usable magnetic particles and particle compositions, the corresponding parts of EP 1224542, WO 2004/091386, WO 2004/091390, WO 2004/091394, WO 2004/091395, WO 2004/091396, WO 2004/091397, WO 2004/091398, WO 2004/091408 are herewith referred to, which are herein incorporated by reference. In these documents more details of the MPI method in general can be found as well.

During the data acquisition, the x-, y-, and z-coil pairs 12, 14, 16 generate a position- and time-dependent magnetic field, the applied field. This is achieved by directing suitable currents through the field generating coils. In effect, the drive and focus fields push the selection field around such that the FFP moves along a preselected FFP trajectory that traces out the volume of scanning—a superset of the field of view. The applied field orientates the magnetic nanoparticles in the patient. As the applied field changes, the resulting magnetization changes too, though it responds nonlinearly to the applied field. The sum of the changing applied field and the changing magnetization induces a time-dependent voltage $V_k$ across the terminals of the receive coil pair along the $x_k$-axis. The associated receiver converts this voltage to a signal $S_k$, which it processes further.

Figure 3:
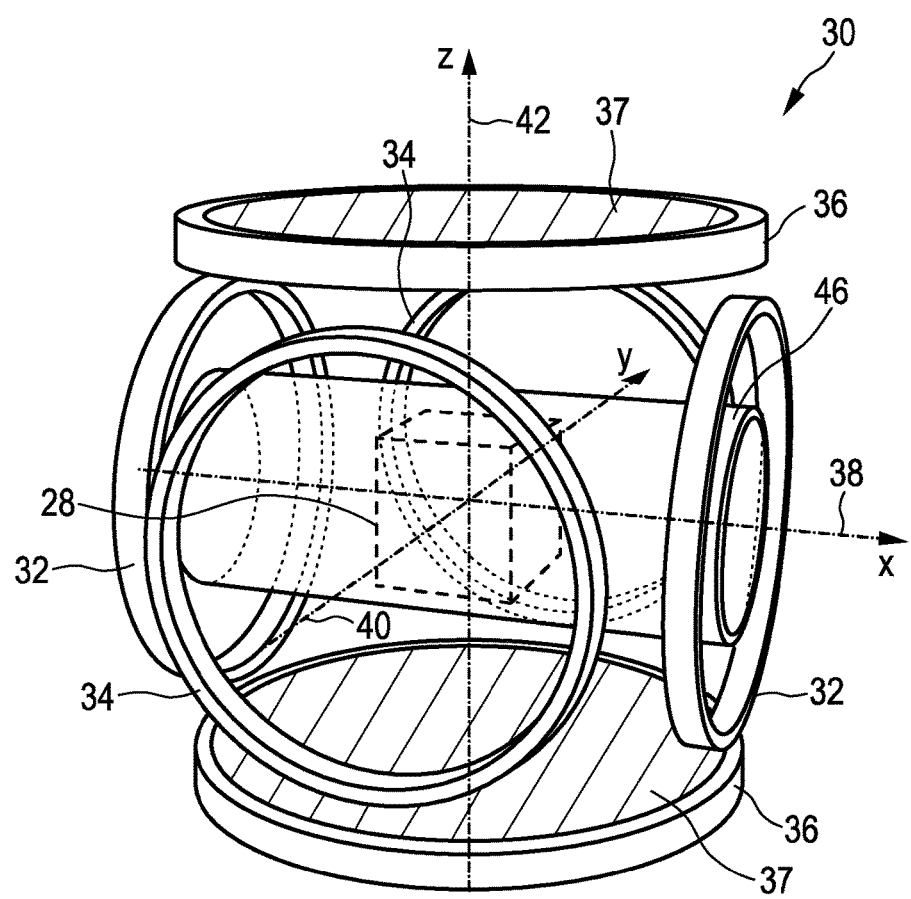
FIG. 3 shows a second embodiment of an MPI apparatus.

Like the first embodiment 10 shown in FIG. 1, the second embodiment 30 of the MPI scanner shown in FIG. 3 has three circular and mutually orthogonal coil pairs 32, 34, 36, but these coil pairs 32, 34, 36 generate the selection field and the focus field only. The z-coils 36, which again generate the selection field, are filled with ferromagnetic material 37. The z-axis 42 of this embodiment 30 is oriented vertically, while the x- and y-axes 38, 40 are oriented horizontally. The bore 46 of the scanner is parallel to the x-axis 38 and, thus, perpendicular to the axis 42 of the selection field. The drive field is generated by a solenoid (not shown) along the x-axis 38 and by pairs of saddle coils (not shown) along the two remaining axes 40, 42. These coils are wound around a tube which forms the bore. The drive field coils also serve as receive coils.

To give a few typical parameters of such an embodiment: The z-gradient of the selection field, G, has a strength of $G/\mu_0 = 2.5$ T/m, where $\mu_0$ is the vacuum permeability. The temporal frequency spectrum of the drive field is concentrated in a narrow band around 25 kHz (up to approximately 150 kHz). The useful frequency spectrum of the received signals lies between 50 kHz and 1 MHz (eventually up to approximately 15 MHz). The bore has a diameter of 120 mm. The biggest cube 28 that fits into the bore 46 has an edge length of 120 mm/$\sqrt{2} \approx 84$ mm.

Since the construction of field generating coils is generally known in the art, e.g. from the static B0 field of magnetic resonance imaging, this subject need not be further elaborated herein.

In an alternative embodiment for the generation of the selection field, permanent magnets (not shown) can be used. In the space between two poles of such (opposing) permanent magnets (not shown) there is formed a magnetic field which is similar to that shown in FIG. 2, that is, when the opposing poles have the same polarity. In another alternative embodiment, the selection field can be generated by a mixture of at least one permanent magnet and at least one coil.

Figure 4A:
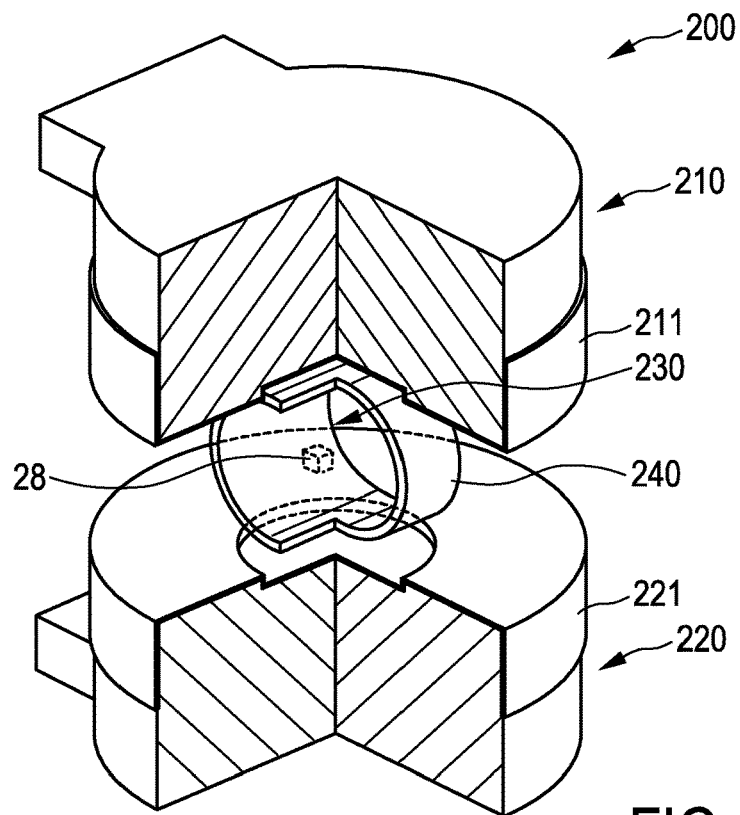
FIG. 4 shows a third and a fourth embodiment of an MPI apparatus.

FIG. 4 shows two embodiments of the general outer layout of an MPI apparatus 200, 300. FIG. 4A shows an embodiment of the proposed MPI apparatus 200 comprising two selection-and-focus field coil units 210, 220 which are basically identical and arranged on opposite sides of the examination area 230 formed between them. Further, a drive field coil unit 240 is arranged between the selection-and-focus field coil units 210, 220, which are placed around the area of interest of the patient (not shown). The selection-and-focus field coil units 210, 220 comprise several selection-and-focus field coils for generating a combined magnetic field representing the above-explained magnetic selection field and magnetic focus field. In particular, each selection-and-focus field coil unit 210, 220 comprises a, preferably identical, set of selection-and-focus field coils. Details of said selection-and-focus field coils will be explained below.

The drive field coil unit 240 comprises a number of drive field coils for generating a magnetic drive field. These drive field coils may comprise several pairs of drive field coils, in particular one pair of drive field coils for generating a magnetic field in each of the three directions in space. In an embodiment the drive field coil unit 240 comprises two pairs of saddle coils for two different directions in space and one solenoid coil for generating a magnetic field in the longitudinal axis of the patient.

The selection-and-focus field coil units 210, 220 are generally mounted to a holding unit (not shown) or the wall of room. Preferably, in case the selection-and-focus field coil units 210, 220 comprise pole shoes for carrying the respective coils, the holding unit does not only mechanically hold the selection-and-focus field coil unit 210, 220 but also provides a path for the magnetic flux that connects the pole shoes of the two selection-and-focus field coil units 210, 220.

As shown in FIG. 4a, the two selection-and-focus field coil units 210, 220 each include a shielding layer 211, 221 for shielding the selection-and-focus field coils from magnetic fields generated by the drive field coils of the drive field coil unit 240.

Figure 4B:
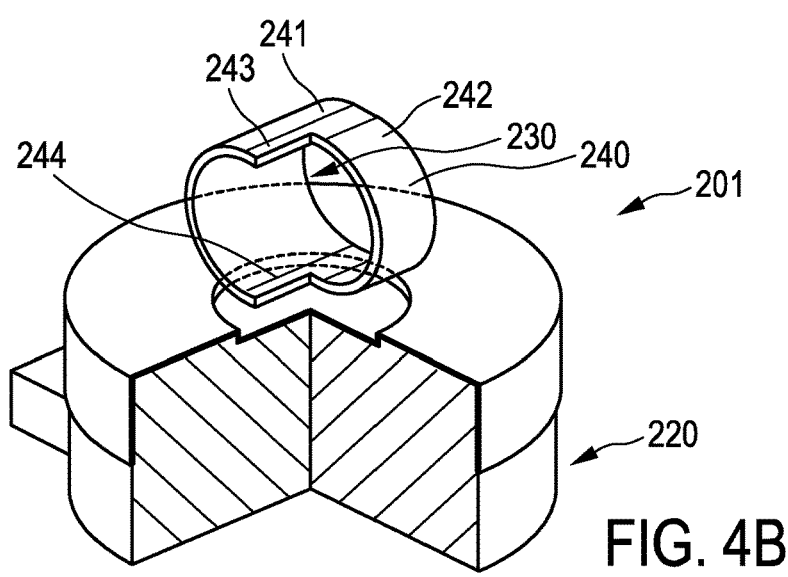

In the embodiment of the MPI apparatus 201 shown in FIG. 4B only a single selection-and-focus field coil unit 220 is provided as well as the drive field coil unit 240. Generally, a single selection-and-focus field coil unit is sufficient for generating the required combined magnetic selection and focus field. Said single selection-and-focus field coil unit 220 may thus be integrated into a (not shown) patient table on which a patient is placed for the examination. Preferably, the drive field coils of the drive field coil unit 240 may be arranged around the patient's body already in advance, e.g. as flexible coil elements. In another implementation, the drive field coil unit 240 can be opened, e.g. separable into two subunits 241, 242 as indicated by the separation lines 243, 244 shown in FIG. 4b in axial direction, so that the patient can be placed in between and the drive field coil subunits 241, 242 can then be coupled together.

In still further embodiments of the MPI apparatus, even more selection-and-focus field coil units may be provided which are preferably arranged according to a uniform distribution around the examination area 230. However, the more selection-and-focus field coil units are used, the more will the accessibility of the examination area for placing a patient therein and for accessing the patient itself during an examination by medical assistance or doctors be limited.

Figure 5:
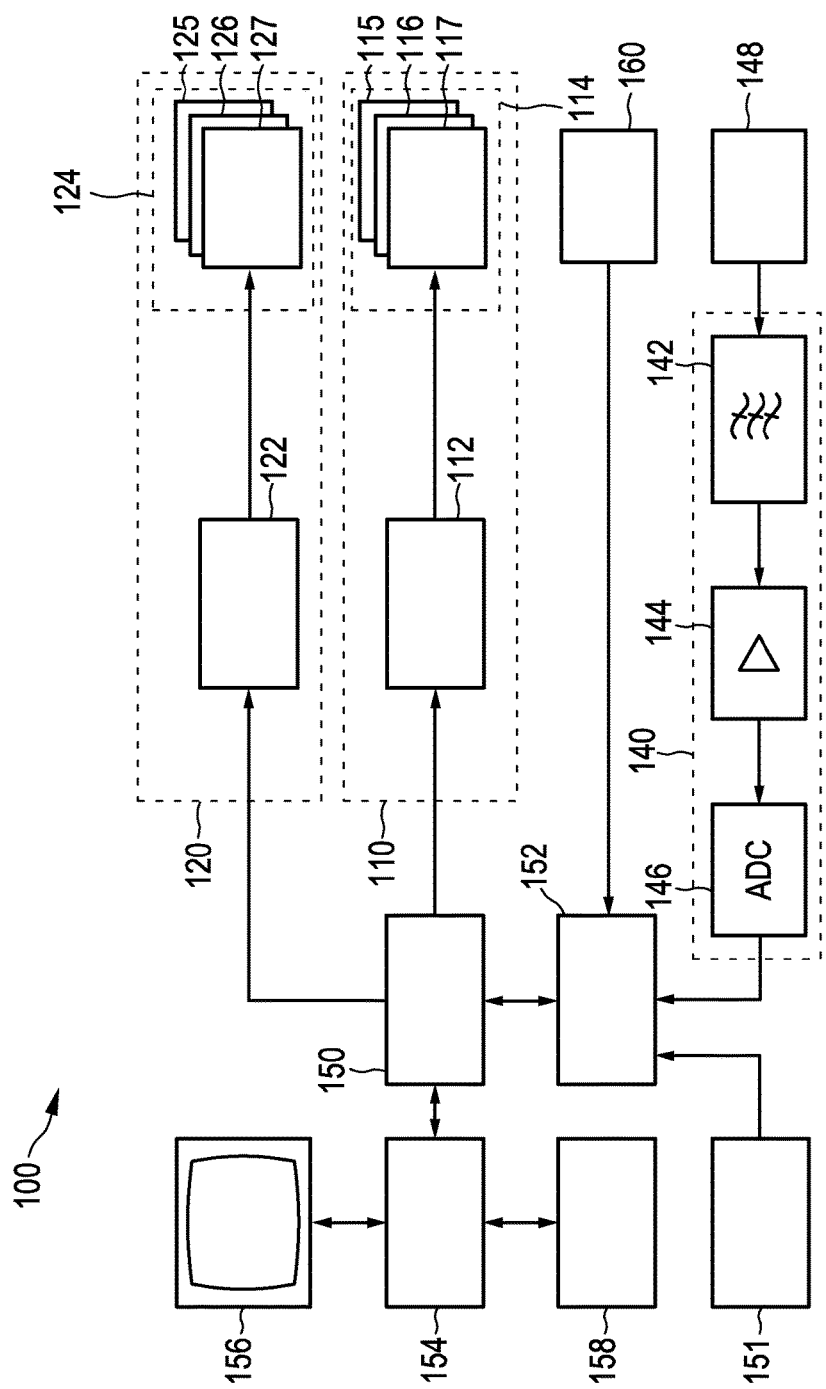
FIG. 5 shows a block diagram of an MPI apparatus according to the present invention.

FIG. 5 shows a general block diagram of an MPI apparatus 100 according to the present invention. The general principles of magnetic particle imaging explained above are valid and applicable to this embodiment as well, unless otherwise specified.

The embodiment of the apparatus 100 shown in FIG. 5 comprises various coils for generating the desired magnetic fields. First, the coils and their functions in MPI shall be explained.

For generating the combined magnetic selection-and-focus field, selection-and-focus elements 110 are provided. The magnetic selection-and-focus field has a pattern in space of its magnetic field strength such that the first sub-zone (52 in FIG. 2) having a low magnetic field strength where the magnetization of the magnetic particles is not saturated and a second sub-zone (54 in FIG. 4) having a higher magnetic field strength where the magnetization of the magnetic particles is saturated are formed in the field of view 28, which is a small part of the examination area 230, which is conventionally achieved by use of the magnetic selection field. Further, by use the magnetic selection-and-focus field the position in space of the field of view 28 within the examination area 230 can be changed, as conventionally done by use of the magnetic focus field.

The selection-and-focus elements 110 comprises at least one set of selection-and-focus field coils 114 and a selection-and-focus field generator unit 112 for generating selection-and-focus field currents to be provided to said at least one set of selection-and-focus field coils 114 (representing one of the selection-and-focus field coil units 210, 220 shown in FIGS. 4A, 4B) for controlling the generation of said magnetic selection-and-focus field. Preferably, a separate generator subunit is provided for each coil element (or each pair of coil elements) of the at least one set of selection-and-focus field coils 114. Said selection-and-focus field generator unit 112 comprises a controllable current source (generally including an amplifier) and a filter unit which provide the respective coil element with the field current to individually set the gradient strength and field strength of the contribution of each coil to the magnetic selection-and-focus field. It shall be noted that the filter unit can also be omitted. In another embodiment separate selection elements and focus elements, i.e. selection field generator unit, focus field generator unit, selection field coils and focus field coils are provided as separate elements.

For generating the magnetic drive field the apparatus 100 further comprises drive elements 120 comprising a drive field signal generator unit 122 and a set of drive field coils 124 (representing the drive coil unit 240 shown in FIGS. 4A, 4B) for changing the position in space and/or size of the two sub-zones in the field of view by means of a magnetic drive field so that the magnetization of the magnetic material changes locally. As mentioned above said drive field coils 124 preferably comprise two pairs 125, 126 of oppositely arranged saddle coils and one solenoid coil 127. Other implementations, e.g. three pairs of coil elements, are also possible.

The drive field signal generator unit 122 preferably comprises a separate drive field signal generation subunit for each coil element (or at least each pair of coil elements) of said set of drive field coils 124. Said drive field signal generator unit 122 preferably comprises a drive field current source (preferably including a current amplifier) and a filter unit (which may also be omitted with the present invention) for providing a time-dependent drive field current to the respective drive field coil.

The selection-and-focus field signal generator unit 112 and the drive field signal generator unit 122 are preferably controlled by a control unit 150, which preferably controls the selection-and-focus field signal generator unit 112 such that the sum of the field strengths and the sum of the gradient strengths of all spatial points of the selection field is set at a predefined level. For this purpose the control unit 150 can also be provided with control instructions by a user according to the desired application of the MPI apparatus, which, however, is preferably omitted according to the present invention.

For using the MPI apparatus 100 for determining the spatial distribution of the magnetic particles in the examination area (or a region of interest in the examination area), particularly to obtain images of said region of interest, signal detection receiving elements 148, in particular a receiving coil, and a signal receiving unit 140, which receives signals detected by said receiving elements 148, are provided. Preferably, three receiving coils 148 and three receiving units 140—one per receiving coil—are provided in practice, but more than three receiving coils and receiving units can be also used, in which case the acquired detection signals are not 3-dimensional but K-dimensional, with K being the number of receiving coils.

Said signal receiving unit 140 comprises a filter unit 142 for filtering the received detection signals. The aim of this filtering is to separate measured values, which are caused by the magnetization in the examination area which is influenced by the change in position of the two part-regions (52, 54), from other, interfering signals. To this end, the filter unit 142 may be designed for example such that signals which have temporal frequencies that are smaller than the temporal frequencies with which the receiving coil 148 is operated, or smaller than twice these temporal frequencies, do not pass the filter unit 142. The signals are then transmitted via an amplifier unit 144 to an analog/digital converter 146 (ADC).

The digitalized signals produced by the analog/digital converter 146 are fed to an image processing unit (also called reconstruction means) 152, which reconstructs the spatial distribution of the magnetic particles from these signals and the respective position which the first part-region 52 of the first magnetic field in the examination area assumed during receipt of the respective signal and which the image processing unit 152 obtains from the control unit 150. The reconstructed spatial distribution of the magnetic particles is finally transmitted via the control means 150 to a computer 154, which displays it on a monitor 156. Thus, an image can be displayed showing the distribution of magnetic particles in the field of view of the examination area.

In other applications of the MPI apparatus 100, e.g. for influencing the magnetic particles (for instance for a hyperthermia treatment) or for moving the magnetic particles (e.g. attached to a catheter for moving the catheter or attached to a medicament for moving the medicament to a certain location) the receiving elements may also be omitted or simply not used.

Further, an input unit 158 may optionally be provided, for example a keyboard. A user may therefore be able to set the desired direction of the highest resolution and in turn receives the respective image of the region of action on the monitor 156. If the critical direction, in which the highest resolution is needed, deviates from the direction set first by the user, the user can still vary the direction manually in order to produce a further image with an improved imaging resolution. This resolution improvement process can also be operated automatically by the control unit 150 and the computer 154. The control unit 150 in this embodiment sets the gradient field in a first direction which is automatically estimated or set as start value by the user. The direction of the gradient field is then varied stepwise until the resolution of the thereby received images, which are compared by the computer 154, is maximal, respectively not improved anymore. The most critical direction can therefore be found respectively adapted automatically in order to receive the highest possible resolution.

For fast coverage of imaging volumes much larger than the volume covered by the drive field excitation, rapid focus field variations can be employed. However, when the resulting spatial shift during one encoding sequence is larger than the reconstructed spatial resolution, image artifacts arise. The present invention compensates for the motion on the data processing side and thus reconstruct images with no or reduced motion artifacts.

For high FOV velocities up to several hundred mm/s artifacts can be reduced by adding a (e.g. linear) shift to the time-domain representation of the static system function used for image reconstruction. The static SF is typically acquired in the absence of variable focus fields and stored in the frequency domain representation in a storage unit 151, e.g. a memory element such as a hard disk or a semiconductor memory. This "static" system function is thus obtained in advance for the particular MPI apparatus and is stored for later use.

In a preferred embodiment of the proposed system and method, during or after the actual data acquisition of detection signals the stored static system function is transformed into the temporal domain via Fourier transformation. Sequential volumes representing different times during the movement of the field-free point (FFP) along the trajectory are then shifted according to the FFP shift induced by the variable focus fields. Afterwards, the obtained extended system function is transformed back to the frequency domain where the standard reconstruction procedure is applied using the obtained extended system function. In this way the rapid shift of the FOV with respect to the encoding period is compensated and artifacts are reduced or even completely avoided.

Any other representation that allows generation of adequate system functions can be used as well (e.g. temporal domain versus Fourier transformed spatial domain, where the shift-correction is performed via the Fourier shift theorem, or temporal versus cosine transformed spatial domain).

The magnetic focus field is generally known to the corresponding generator unit and/or control unit so that the processing unit 152 can determine the movement of the FFP caused by application of the magnetic focus field and can thus calculate necessary shift of the static system function to obtain the extended system function. However, to also compensate for eddy currents, in other embodiments measurement means 160 are provided for measuring the magnetic focus field, wherein said processing elements 152 is configured to use the measured magnetic focus field for shifting the time-domain representation of said static system function proportional to the changes of the position of the field of view caused by the measured magnetic focus field. Said measurement means preferably include a Hall sensor.

FIG. 6 shows a diagram illustrating two views of a Lissajous trajectory (which encodes one volume or FOV) without and after applying a linear diagonal shift. FIG. 6 particularly shows how the FFP path changes when the course of one 3D Lissajous cycle is superimposed with a fast translational motion at constant velocity. FIG. 6A shows a top view and FIG. 6B shows an oblique view of the original Lissajous trajectory. FIG. 6C shows a top view and FIG. 6D shows an oblique view of the Lissajous trajectory after a linear diagonal shift is applied showing that the Lissajous trajectory is dispersed over a larger volume. For reconstruction, the individual volumes of the static time-domain representation of the static system function are shifted accordingly. This is depicted in FIG. 7.

FIG. 7 shows a diagram of several time-domain representations of a static system function without and with interpolation/padding for obtaining an extended system function. In particular, FIGS. 7A, 7B, 7C show different time frames of a measured static system function and FIGS. 7D, 7E, 7F show different time frames of a generated extended system function obtained by applying the linear diagonal shift applied to the Lissajous trajectory to the respective time frames of the static system function. As can be seen the volume covered by the extended system function is larger and the position of the respective time frames of the static system function within said larger volume changes from time frame to time frame. This larger volume is preferably obtained by padding and/or interpolating in the direction of motion. Preferably, the respective time frames of the static system function are copied into the time frames of the larger volume at the correct spatial position and the remaining volume is filled with zeros (or with extrapolated voxels). In this example, the padded voxels are filled with zeros. However, to reduce artifacts, the remaining voxels are filled with values extrapolated from the neighboring measured values, e.g. with a smooth decay towards to edges of the volume.

The above described embodiment of acquiring a static system function, which is later ("on the fly") modified according to the actually applied movement of the field of view in response to the application of a focus field provides the advantage that this allows to flexibly deal with different shift directions and velocities.

Generally, not only linear shifts, but also accelerated and/or curved motions can be compensated, if the field evolution is known. To minimize space-dependent field distortions, the static system function should have been measured close to the position where the object data (i.e. the detection data) is acquired.

Figure 6A:
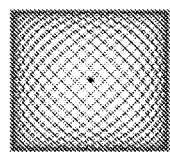
FIG. 6 shows a diagram illustrating two views of a Lissajous trajectory without and after applying a linear diagonal shift.
Figure 6C:
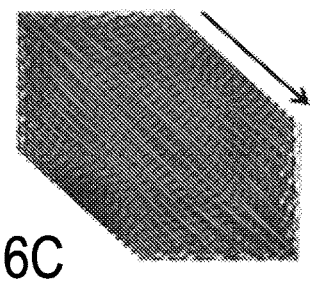
Figure 6B:
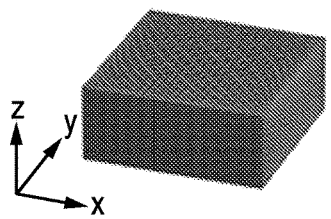
Figure 6D:
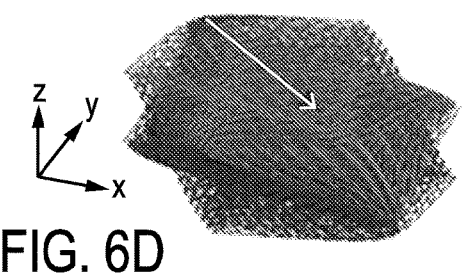
Figure 7A:
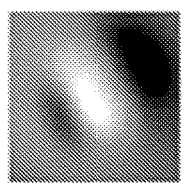
FIG. 7 shows a diagram of several time-domain representations of a static system function without and with interpolation/padding for obtaining an extended system function.
Figure 7B:
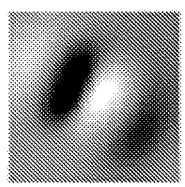
Figure 7C:
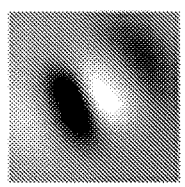
Figure 7D:
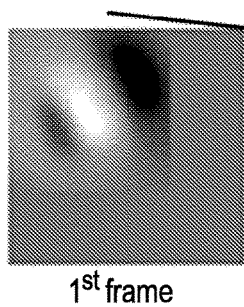
Figure 7E:
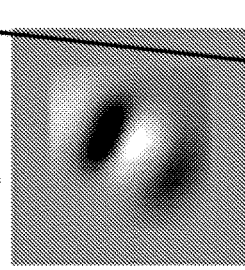
Figure 7F:
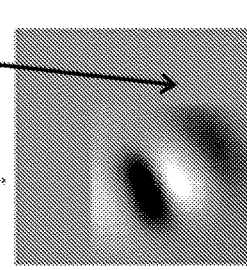

In FIGS. 6C and 6D it can be seen that the extended FOV is no longer covered homogeneously. To have an object fully covered by the FFP path during one Lissajous cycle, it is proposed in a further embodiment to shift the starting and end point of the reconstructed trajectory. For instance, if the object is covered by the last half of a cycle and the first half of the next cycle, a time shift of half a Lissajous cycle puts the object to the center of a reconstructed volume. For instance, if a spatial shift is made that extends over several Lissajous cycles, it may be preferred not to reconstruct one trajectory from t=0 to t=TR (TR being the duration of a cycle), but a later part from e.g. t=TR/2 to t=3*TR/2, for instance, because during this later time portion the sampling of the object (i.e. spatial coverage) may be better. It is further possible to reconstruct arbitrary time portions from t=a*TR to t=b*TR with a<b.

Thus, different time shifts can be reconstructed to find the optimum. In addition, it can be useful to concatenate shifted (extended) system functions and the respective object time signal, with the aim of reconstructing larger volumes in a single step. The time representations of the shifted (extended) system functions are thus arranged in sequence in accordance with the sequence of the acquisition of the detection signals. An arbitrarily long extended system functions can be formed in this way.

If the applied shift is very fast, large gaps may occur between the paths covered by the FFP. This can degrade local spatial resolution. Thus, in another embodiment an algorithm is applied to determine the size and position of the largest gaps for a given focus field shift. This information can be indicated to the user as a warning (e.g. in case of a too large or misplaced gap) that slower or other focus field variations should be chosen. More generally, a map representing some measure of trajectory density can be displayed along with the images to indicate local image quality.

If the shift-corrected (extended) system function extends far beyond the position it was measured at, off-center field distortions (deviation from constant selection field gradient, inhomogeneities in focus and drive fields) are taken into account in an embodiment. Using simulated or experimentally determined field maps, an adequate distortion correction is applied to the reconstructed images according to another embodiment. Furthermore, dynamic field distortions arising from eddy currents can be measured or modeled and then applied for correction of time-dependent image distortions.

Since the absolute FFP velocity is slightly changed by the addition of dynamic focus fields to the drive fields, the spatial signal response patterns are not only shifted, but also slightly modified in amplitude. To compensate for that, an amplitude correction based on the absolute FFP velocity (focus+drive field effect) is introduced according to a preferred embodiment. The signal strength is substantially proportional to the velocity of the FFP. In this case the signal difference between the two situations (dynamic vs. static) may be retrieved from a simulation or a measurement.

In still another embodiment not only a single static system function is obtained and stored in advance, but several static system functions for different positions of the field of view and/or several extended system functions are obtained already with the additional translational motion, i.e. a plurality of extended system functions are obtained in advance (preferably, extended system functions are obtained for typical combinations of magnetic drive fields and magnetic focus fields) while different magnetic focus fields are applied. In other words, as one option a plurality of extended system functions are generated by shifting the time-domain representation of a static system function proportional to different changes of the position of the field of view caused by appliance of different magnetic focus fields or are obtained while different changes of the position of the field of view are caused by appliance of different magnetic focus fields.

In this case the knowledge of the magnetic focus field may be used for selecting or constructing the optimal extended system function. In another embodiment measurement means 160 (e.g. a Hall sensor) may be provided for measuring the magnetic focus field, wherein said processing elements 152 is configured to use the measured magnetic focus field for selecting or constructing an extended system function from the stored plurality of extended system functions.

Thus, in an embodiment the most appropriate extended system function may be constructed (or assembled) from the catalogue of previously acquired static and/or extended system functions. For instance, for each time portion of the trajectory, a system function can be searched, which has a similar progress for a comparable time portion, which portion can be used in the extended system function. The length of the time portion should be in the range of the magnetic relaxation times. The portions are then arranged subsequently (possibly with cross-fading) to form the finally desired extended system function.

The time-domain system function can be seen as a catalogue of point-spread functions (PSFs) occurring for various different field-free point motion directions. Ideally, from this catalogue, all PSFs necessary for reconstructing data from an arbitrary trajectory can be collected and combined into an adequate system function. To compensate for different spatial positions of the FFP, the PSFs have to be shifted accordingly. Also, since the PSF amplitude depends on the FFP speed, the catalogue should either contain the PSFs for different speeds or an amplitude correction for different speeds should be introduced. Furthermore, for non-Langevin particles, the FFP motion history influences the PSF at a certain point in time. Thus, the pre-history over a certain time period (typically defined by magnetic relaxation times) should be known to compensate for its influence.

A simple implementation of this catalogue approach is to measure the catalogue (i.e. the system function) for a trajectory that closely resembles the trajectory used for the object measurement. For example, one or more static system functions obtained in the absence of focus fields can be used as a catalogue for generating extended system functions for the reconstruction of data acquired in the presence of focus field variations. In this simple implementation, the catalogue is represented in the temporal versus spatial domain. However, any other representation that allows generation of adequate system functions can be used (e.g. temporal domain versus Fourier transformed spatial domain, where the shift-correction is performed via the Fourier shift theorem, or temporal versus cosine transformed spatial domain).

Measurements were performed using an experimental pre-clinical demonstrator system. Three orthogonal drive fields were applied at amplitude 16 mT and at frequencies 24.5, 26.0, and 25.3 kHz for the x, y, and z channel, respectively. Permanent magnets generate selection field gradients of $dBx/dx=dBy/dy=1.25$ T/m and $dBz/dz=2.50$ T/m, so that the drive fields encode a FOV of $25.6\times25.6\times12.8$ mm$^3$. For imaging, a phantom consisting of 5 parallel tubes was filled with Resovist at a dilution of 1:10, corresponding to a concentration of 50 mmol(Fe)/l. Volumes were acquired at a rate of 46.4 Hz. For image reconstruction, a system function was determined in a calibration scan, where the response of a small cylindrical sample (l=2 mm, Ø=1 mm) of pure Resovist was recorded on a rectangular grid of dimension $30\times30\times20$ with a spacing of $1.2\times1.2\times1.0$ mm$^3$. During imaging, the focus fields were swept at rates corresponding to FOV shift velocities of roughly 33, 66, 132, 264, 528, 1056, 2112, and 4224 mm/s, respectively. The focus fields were changed on the x and y channel simultaneously, resulting in a diagonal sweep of the FOV over the static phantom.

Figures 8A, 8B, 8C:
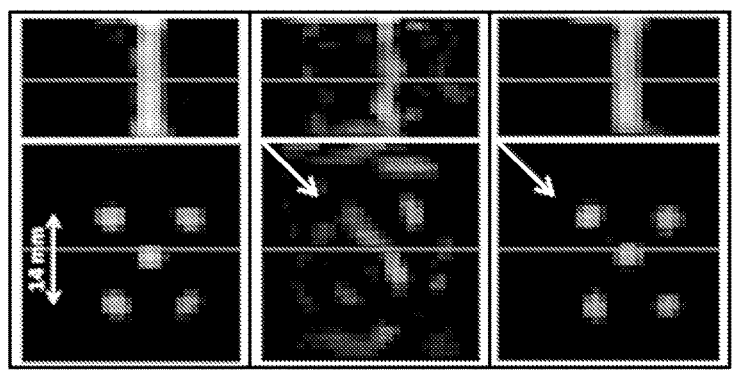
FIG. 8 shows orthogonal slices from 3D volumes of a phantom obtained with slow focus field motion and with fast focus field motion (with and without use of the present invention).

FIG. 8 shows orthogonal slices from one volume during the sweep over the phantom. For FIG. 8A the shift per encoding time (0.7 mm for a velocity of 33 mm/s) remains below the resolution, while for FIG. 8B it is about a factor of 20 above the resolution (22.7 mm for a velocity of 1056 mm/s), leading to massive image artifacts. FIG. 8C shows the reconstruction using a system function that has been adapted by spatially shifting the time-domain signal response proportionally to the FOV shift during one encoding period. By this measure, the artifacts are almost completely removed.

In conclusion, when shifting the FOV during imaging, artifacts arise when the shift per volume encoding time is larger than the resolution. Up to shift velocities of about 1 m/s, these can be removed by compensating the system function for the rapid translation. Fast continuous FOV shifts may be used to rapidly steer a single imaging volume to a region of interest or to achieve large spatial coverage by repeatedly sweeping the FOV through a volume of interest.

The proposed invention allows imaging while the focus of the imaging volume is rapidly moved in space. This allows the implementation of focus field sequences that employ variable fields, e.g. with constant rates of change (constant FOV shift velocities) or sinusoidal field variations, with the aim of covering large volumes in a short amount of time. In addition, the method can be used in multi-station imaging (as e.g. described in J. Rahmer et al., "Results on Rapid 3D Magnetic Particle Imaging with a Large Field of View.", Proc. ISMRM, 19:629, 2011) to generate images from the time intervals during which the focus is moved between the stations and which to date had to be discarded. Thus, all acquired information can be used to optimize SNR and temporal resolution.

The method of adapting the system function to the shift applies to the general case of relative motion between the FOV and the object, i.e. if the FOV is static but the object moves rapidly, the same correction can be applied.

The various above explained ideas can each be used independently for single or all drive field coils, but are preferably used together in a preferred embodiment of an MPI apparatus according to the present invention.

The reference to a Lissajous trajectory in the above shall be understood as an example only. The invention may also be applied when other trajectories are used.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An apparatus for influencing and/or detecting magnetic particles in a field of view comprising:

selection elements, the selection elements comprising a selection field signal generator unit and selection field elements, wherein the selection field elements are arranged to generate a magnetic selection field, the magnetic selection field having a pattern in space of its magnetic field strength in the field of view,
   wherein, in a first sub-zone of the space, the magnetization of the magnetic particles is not saturated,
   wherein, in a second sub-zone of the space, the magnetization of the magnetic particles is saturated,
drive elements comprising a drive field signal generator unit and drive field coils,
   wherein the drive field coils are arranged to change a position in space of the first and second sub-zones in the field of view using a magnetic drive field so that the magnetization of the magnetic material changes locally, focus elements comprising a focus field signal generator unit and one or more focus field elements,
wherein the focus field elements are arranged to change a position in space of the field of view using a magnetic focus field,
receiving elements arranged to acquire detection signals,
wherein the detection signals depend on the magnetization in the field of view,
wherein the magnetization in the field of view is influenced by the change in the position in space of the first and second sub-zone,
storage elements for storing a static system function of the apparatus obtained in the absence of the magnetic focus field,
processing elements for generating an extended system function by shifting a time-domain representation of the static system function in proportion to the changes of the position of the field of view caused by appliance of the magnetic focus field,
wherein the processing elements reconstruct the spatial distribution of the magnetic particles in the field of view using the detection signals and the extended system function.

2. The apparatus as claimed in claim 1,
wherein the storage elements are configured to store a frequency-domain representation of the static system function, and
wherein the processing elements are configured to convert the frequency-domain representation of the static system function into the time-domain representation before shifting the time-domain representation of the static system function to generate the extended system function and to convert the extended system function into a frequency-domain representation
wherein the frequency-domain representation is then used for reconstructing the spatial distribution of the magnetic particles.

3. The apparatus as claimed in claim 1, further comprising measurement elements,
wherein the measuring elements measure the magnetic focus field,
wherein the processing elements are configured to use the measured magnetic focus field for shifting the time-domain representation of the static system function in proportion to the changes of the position of the field of view caused by the measured magnetic focus field.

4. The apparatus as claimed in claim 1,
wherein the processing elements are configured to generate the extended system function by padding in the direction of motion of the magnetic focus field,
wherein padded voxels are filled with zeros or with extrapolated values of the values of neighboring voxels.

5. An apparatus for influencing and/or detecting magnetic particles in a field of view comprising:
selection elements, the selection elements comprising a selection field signal generator unit and selection field elements, wherein the selection field elements are arranged to generate a magnetic selection field, the magnetic selection field having a pattern in space of its magnetic field strength in the field of view,
wherein, in a first sub-zone of the space, the magnetization of the magnetic particles is not saturated,
wherein, in a second sub-zone of the space, the magnetization of the magnetic particles is saturated,
drive elements comprising a drive field signal generator unit and drive field coils
wherein the drive field coils are arranged to change a position in space of the first and second sub-zones in the field of view using a magnetic drive field so that the magnetization of the magnetic material changes locally,
focus elements comprising a focus field signal generator unit and one or more focus field elements,
wherein the focus field elements are arranged to change a position in space of the field of view using a magnetic focus field,
receiving elements arranged to acquire detection signals,
wherein the detection signals depend on the magnetization in the field of view,
wherein the magnetization is influenced by the change in the position in space of the first and second sub-zone,
storage elements for storing a plurality of static and/or extended system functions of the apparatus,
wherein the static system functions have been obtained in the absence of the magnetic focus field at different positions of the field of view,
wherein the extended system functions have been generated by shifting the time-domain representation of a static system function proportional to different changes of the position of the field of view caused by an application of different magnetic focus fields or have been obtained while different changes of the position of the field of view are caused by an application of different magnetic focus fields, and
processing elements for reconstructing the spatial distribution of the magnetic particles in the field of view from the detection signals and an extended system function selected from a plurality of stored extended system functions or constructed from one or more of a plurality of stored static and/or extended system functions based on the magnetic focus field applied for changing the position in space of the field of view.

6. The apparatus as claimed in claim 5, wherein an extended system function is generated by shifting a time-domain representation of at least one of the static system functions of the apparatus obtained in the absence of the magnetic focus field proportional to the changes of the position of the field of view caused by appliance of the magnetic focus field.

7. The apparatus as claimed in claim 5, further comprising measurement elements for measuring the magnetic focus field, wherein the processing elements are configured to use the measured magnetic focus field for selecting or constructing an extended system function from the stored plurality of static and/or extended system functions.

8. The apparatus as claimed in claim 5, wherein the storage elements are configured to store a plurality of extended system functions that have been obtained for different speeds of movement of the first sub-zone, and/or different directions of movement of the first sub-zone and/or different trajectories along which the first sub-zone is moved.

9. The apparatus as claimed in claim 3, wherein the measurement elements comprise one or more Hall sensors.

10. The apparatus as claimed in claim 1, wherein the changes of the position of the field of view caused by an application of the magnetic focus field compensated by shifting a time-domain representation of the static system function includes one or more of a linear shift motion, an accelerated motion, a decelerated motion and a curved motion.

11. The apparatus as claimed in claim 1,
wherein the processing elements are configured to shift the starting and/or end point of a reconstructed trajectory,
wherein different time shifts are reconstructed
wherein extended system functions are concatenated.

12. The apparatus as claimed in claim 1, wherein the processing elements are configured to determine the size and position of the largest gaps between paths of the trajectory covered by the first sub-zone.

13. The apparatus as claimed in claim 1, wherein the processing elements are configured to apply a distortion correction to the reconstructed spatial distribution of the magnetic particles and/or to apply an amplitude correction of the amplitude of the extended system function based on the velocity of the movement of the first sub-zone during appliance of the magnetic focus field.

14. A method for influencing and/or detecting magnetic particles in a field of view, which method comprises:
generating a magnetic selection field, the magnetic selection field having a pattern in space of its magnetic field strength in the field of view,
wherein, in a first sub-zone of the space, the magnetization of the magnetic particles is not saturated,
wherein, in a second sub-zone of the space, the magnetization of the magnetic particles is saturated,
changing the position in space of the two sub-zones in the field of view using a magnetic drive field so that the magnetization of the magnetic material changes locally,
changing the position in space of the field of view using a magnetic focus field, acquiring detection signals,
wherein the detection signals depend on the magnetization in the field of view,
wherein the magnetization is influenced by one or more changes in the position in space of the first and second sub-zone,
storing a static system function of the apparatus obtained in the absence of a magnetic focus field,
generating an extended system function by shifting a time-domain representation of the static system function in proportion to the changes of the position of the field of view,
wherein the changes in the position of the field of view are caused by an application of the magnetic focus field,
wherein the processing elements reconstruct the spatial distribution of the magnetic particles in the field of view from the detection signals and the extended system function.

15. A method for influencing and/or detecting magnetic particles in a field of view, the method comprising:
generating a magnetic selection field, the magnetic selection field having a pattern in space of its magnetic field strength in the field of view,
wherein, in a first sub-zone of the space, the magnetization of the magnetic particles is not saturated,
wherein, in a second sub-zone of the space, the magnetization of the magnetic particles is saturated,
changing the position in space of the two sub-zones in the field of view using a magnetic drive field so that the magnetization of the magnetic material changes locally,
changing the position in space of the field of view using a magnetic focus field,
acquiring detection signals,
wherein the detection signals depend on the magnetization in the field of view,
wherein the magnetization is influenced by one or more changes in the position in space of the first and second sub-zone,
storing a plurality of static and/or extended system functions of the apparatus,
wherein the static system functions are obtained in the absence of a magnetic focus field at different positions of the field of view,
wherein the extended system functions are generated by shifting the time-domain representation of a static system function in proportion to different changes of the position of the field of view caused by an application of different magnetic focus fields or have been obtained while different changes of the position of the field of view are caused by appliance of different magnetic focus fields, and
reconstructing the spatial distribution of the magnetic particles in the field of view from the detection signals and an extended system function selected from a plurality of stored extended system functions or constructed from one or more of a plurality of stored static and/or extended system functions based on the magnetic focus field applied for changing the position in space of the field of view.

16. A non-transitory computer readable medium comprising program code elements for causing a computer to carry out the steps of the method as claimed in claim 14 when the computer program is carried out on the computer.

17. The apparatus as claimed in claim 7, wherein the measurement elements comprise one or more Hall sensors.

18. The apparatus as claimed in claim 5, wherein the changes of the position of the field of view caused by an application of the magnetic focus field compensated by shifting a time-domain representation of the static system function includes one or more of a linear shift motion, an accelerated motion, a decelerated motion and a curved motion.

19. The apparatus as claimed in claim 5,
wherein the processing elements are configured to shift the starting and/or end point of a reconstructed trajectory,
wherein different time shifts are reconstructed, wherein extended system functions are concatenated.

20. The apparatus as claimed in claim 5, wherein the processing elements are configured to determine the size and position of the largest gaps between paths of the trajectory covered by the first sub-zone.

21. The apparatus as claimed in claim 5, wherein the processing elements are configured to apply a distortion correction to the reconstructed spatial distribution of the magnetic particles and/or to apply an amplitude correction of the amplitude of the extended system function based on the velocity of the movement of the first sub-zone during appliance of the magnetic focus field.

* * * * *